(12) United States Patent
Schmidt-Foerst et al.

(10) Patent No.: US 9,610,201 B2
(45) Date of Patent: Apr. 4, 2017

(54) TAMPON HAVING MULTIPLE ABSORBENT REGIONS

(75) Inventors: Alexander Schmidt-Foerst, Erlangen (DE); Mary L. McDaniel, Appleton, WI (US); Charles R. Tomsovic, Omro, WI (US); Garry R. Woltman, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1029 days.

(21) Appl. No.: 13/460,157

(22) Filed: Apr. 30, 2012

(65) Prior Publication Data

US 2012/0283684 A1 Nov. 8, 2012

Related U.S. Application Data

(60) Provisional application No. 61/482,883, filed on May 5, 2011.

(51) Int. Cl.
*A61F 13/15* (2006.01)
*A61F 13/20* (2006.01)

(52) U.S. Cl.
CPC ........ *A61F 13/208* (2013.01); *A61F 13/2028* (2013.01); *A61F 13/2051* (2013.01);
(Continued)

(58) Field of Classification Search
USPC .............................. 604/385.17, 385.18, 904
See application file for complete search history.

(56) References Cited

U.S. PATENT DOCUMENTS 2,330,257 A 9/1943 Bailey
2,858,831 A 11/1958 Graham
(Continued)

FOREIGN PATENT DOCUMENTS

DE 200 21 471 U1 8/2001
EM 000833116-0039 11/2007
(Continued)

OTHER PUBLICATIONS

Five photographs showing tampon, wrapper, and front, back, and bottom views of packaging for Be Easy™ tampons manufactured by Btampon International, Switzerland, and obtained at the INDEX 11 Nonwovens Exhibition held in Geneva, Switzerland, Apr. 12-15, 2011.

(Continued)

*Primary Examiner* — Michele M Kidwell
(74) *Attorney, Agent, or Firm* — Kimberly-Clark Worldwide, Inc.

(57) ABSTRACT

A tampon absorbent for insertion into a vaginal cavity is provided. The tampon absorbent includes a longitudinal direction and has an insertion end and a withdrawal end. The tampon absorbent includes a first absorbent material portion at the insertion end for capturing body fluid and demonstrating a first expansion capacity, and a second absorbent material portion at the withdrawal end for storing body fluid and demonstrating a second expansion capacity. The second absorbent material portion is partially wrapped around the first absorbent material portion in a direction transverse (perpendicular) to the longitudinal direction, at a bonding region, whereby the first absorbent material portion is bonded to the second absorbent material portion at the bonding region.

6 Claims, 9 Drawing Sheets

(52) U.S. Cl.
CPC ...... *A61F 13/2062* (2013.01); *A61F 13/2065* (2013.01); *A61F 13/2068* (2013.01); *A61F 13/2077* (2013.01); *A61F 13/2088* (2013.01); *A61F 13/2094* (2013.01)

(56) References Cited

U.S. PATENT DOCUMENTS

| | | | |
|---|---|---|---|
| 3,038,214 A | | 6/1962 | Griswold et al. |
| 3,084,689 A | * | 4/1963 | Dankwardt et al. .......... 604/286 |
| 3,572,341 A | | 3/1971 | Glassman |
| 3,854,481 A | | 12/1974 | Messing |
| 3,965,905 A | * | 6/1976 | Schoenholz et al. ........... 604/15 |
| 3,971,378 A | | 7/1976 | Krantz |
| 4,217,900 A | | 8/1980 | Klein et al. |
| 4,816,100 A | | 3/1989 | Friese |
| 5,047,024 A | | 9/1991 | Glassman |
| 5,185,010 A | | 2/1993 | Brown |
| 5,364,383 A | | 11/1994 | Hayes et al. |
| 5,533,990 A | | 7/1996 | Yeo |
| 5,542,914 A | * | 8/1996 | Van Iten .......................... 604/11 |
| 5,609,586 A | | 3/1997 | Zadini et al. |
| 5,772,645 A | | 6/1998 | Zadini et al. |
| 6,177,608 B1 | | 1/2001 | Weinstrauch |
| 6,186,994 B1 | | 2/2001 | Bowles et al. |
| 6,186,995 B1 | | 2/2001 | Tharpe |
| 6,258,075 B1 | * | 7/2001 | Taylor et al. ............ 604/385.18 |
| 6,310,269 B1 | | 10/2001 | Friese et al. |
| 6,599,279 B2 | | 7/2003 | Taylor et al. |
| 6,635,800 B2 | * | 10/2003 | Jackson et al. ................ 604/378 |
| 6,740,070 B2 | | 5/2004 | Agyapong et al. |
| 6,758,839 B2 | | 7/2004 | Lochte et al. |
| 6,837,882 B2 | | 1/2005 | Agyapong et al. |
| 6,932,805 B2 | | 8/2005 | Domeier et al. |
| 6,972,010 B2 | | 12/2005 | Pesce et al. |
| 7,338,483 B2 | | 3/2008 | Carlin et al. |
| 7,677,189 B2 | | 3/2010 | Kondo et al. |
| 2002/0156343 A1 | | 10/2002 | Zunker |
| 2002/0183681 A1 | * | 12/2002 | Bernard .......................... 604/15 |
| 2003/0229328 A1 | | 12/2003 | Costa |
| 2003/0233742 A1 | | 12/2003 | Jones et al. |
| 2004/0019317 A1 | * | 1/2004 | Takagi et al. .................... 604/11 |
| 2004/0225272 A1 | | 11/2004 | Karapasha et al. |
| 2005/0096620 A1 | | 5/2005 | Awolin et al. |
| 2005/0096621 A1 | | 5/2005 | Almond |
| 2005/0096622 A1 | | 5/2005 | Almond |
| 2005/0113780 A1 | | 5/2005 | Gatto et al. |
| 2006/0167429 A1 | | 7/2006 | Denti et al. |
| 2006/0247592 A1 | | 11/2006 | Schmidt-Forst et al. |
| 2008/0132868 A1 | | 6/2008 | Jorgensen et al. |
| 2008/0154174 A1 | | 6/2008 | Costa |
| 2008/0154222 A1 | | 6/2008 | Chaffringeon |
| 2008/0262463 A1 | | 10/2008 | Noel et al. |
| 2009/0036857 A1 | | 2/2009 | Sherrod |
| 2009/0036859 A1 | | 2/2009 | Dougherty, Jr. et al. |
| 2010/0114054 A1 | | 5/2010 | Mueller et al. |
| 2011/0092940 A1 | | 4/2011 | Fung et al. |

FOREIGN PATENT DOCUMENTS

| | | |
|---|---|---|
| EM | 000833116-0050 | 11/2007 |
| EP | 0 189 102 A2 | 7/1986 |
| EP | 0 493 728 A1 | 7/1992 |
| EP | 1 250 940 A1 | 10/2002 |
| EP | 0 611 562 B2 | 1/2003 |
| EP | 1 481 656 A1 | 12/2004 |
| EP | 1 547 554 A1 | 6/2005 |
| EP | 1 683 503 A1 | 7/2006 |
| EP | 2 184 044 A1 | 5/2010 |
| JP | 2003-070835 A | 3/2003 |
| JP | 2004-097304 A | 4/2004 |
| WO | WO 89/01062 A1 | 2/1989 |
| WO | WO 98/10133 A1 | 3/1998 |
| WO | WO 00/13638 A2 | 3/2000 |
| WO | WO 00/61052 A1 | 10/2000 |
| WO | WO 01/01910 A1 | 1/2001 |
| WO | WO 01/24729 A2 | 4/2001 |
| WO | WO 01/43679 A1 | 6/2001 |
| WO | WO 01/93794 A1 | 12/2001 |
| WO | WO 02/056793 A2 | 7/2002 |
| WO | WO 02/058587 A2 | 8/2002 |
| WO | WO 02/058613 A1 | 8/2002 |
| WO | WO 02/078587 A1 | 10/2002 |
| WO | WO 03/043556 A2 | 5/2003 |
| WO | WO 03/043558 A2 | 5/2003 |
| WO | WO 03/055429 A1 | 7/2003 |
| WO | WO 2004/030593 A1 | 4/2004 |
| WO | WO 2004/082546 A1 | 9/2004 |
| WO | WO 2005/025474 A1 | 3/2005 |
| WO | WO 2005/041833 A1 | 5/2005 |
| WO | WO 2005/044165 A1 | 5/2005 |
| WO | WO 2006/005069 A1 | 1/2006 |
| WO | WO 2006/015203 A1 | 2/2006 |
| WO | WO 2006/015204 A2 | 2/2006 |
| WO | WO 2007/001216 A1 | 1/2007 |
| WO | WO 2007/038535 A1 | 4/2007 |
| WO | WO 2007/078413 A1 | 7/2007 |
| WO | WO 2009/137383 A1 | 11/2009 |

OTHER PUBLICATIONS

Seven (7) frames of a video entitled "Be Easy: the 1st deluxe tampon," uploaded to YouTube by Btampon on Jun. 29, 2011, Internet web page "http://www.youtube.com/watch?v=bZg8sALvceo".

Seven (7) frames of a video entitled "Be Easy & son usine de production de tampons hygiénigues," uploaded to YouTube by Btampon on May 18, 2011, Internet web page "http://www.youtube.com/watch?v=7HOaM7grAZs&feature=relmfu".

Three (3) frames of a video about Be Easy™ tampons entitled "Btampon International SA—Institutional Reportage," uploaded to YouTube by Btampon on Jan. 4, 2011, Internet web page "http://www.youtube.com/watch?v=tzSb0Gc4o88&feature=relmfu".

Be Easy: échantillon gratuit du nouveau tampon Be Easy, Internet web page "http://www.hellocoton.fr/be-easy-echantillon-gratuit-du-nouveau-tampon-be-easy-2039558", dated Jan. 10, 2011, viewed and printed on Aug. 7,2012, with added machine translation of paragraph at bottom of p. 1, pp. 1-6.

Be Easy: échantillon gratuit du nouveau tampon Be Easy, Internet web page "http://www.echantillons-gratuit.com/be-easy-echantillon-gratuit.html" with comments dated Apr. 21, 2011 through Apr. 26, 2012, viewed and printed Aug. 7, 2012, pp. 1-4.

* cited by examiner

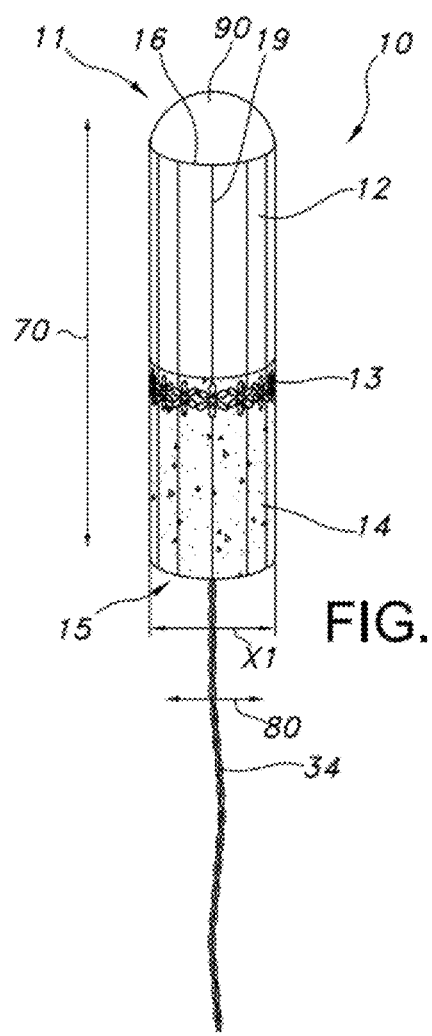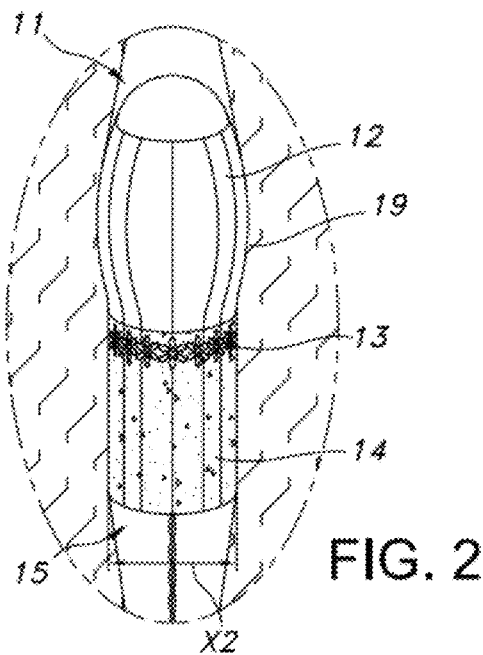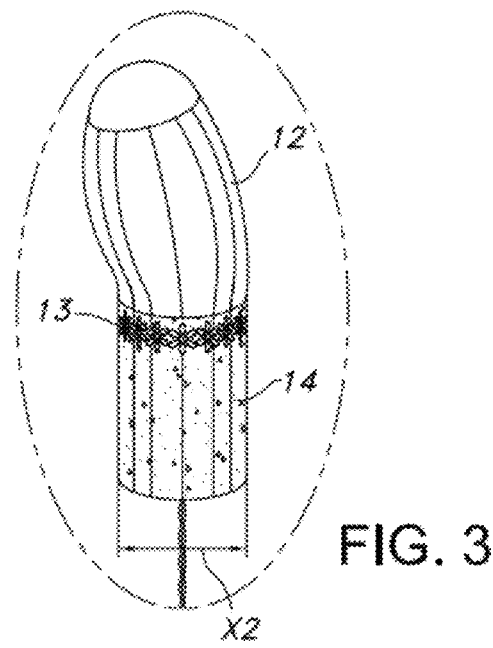

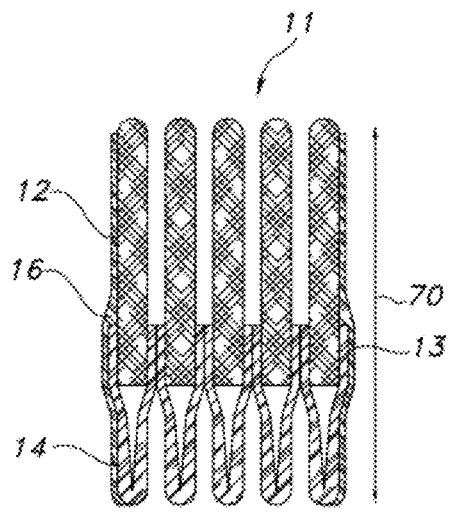
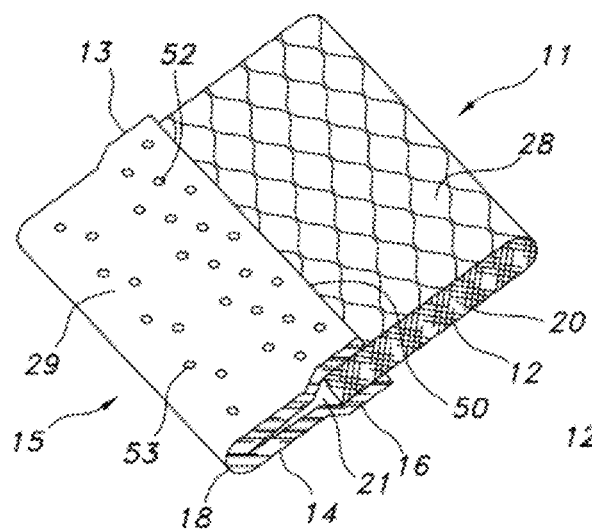
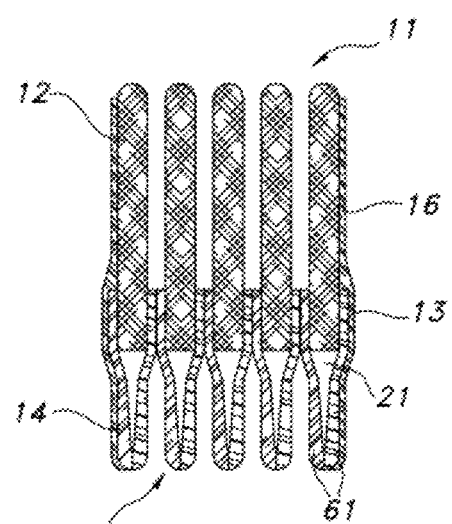
FIG. 6
FIG. 5A
FIG. 7A

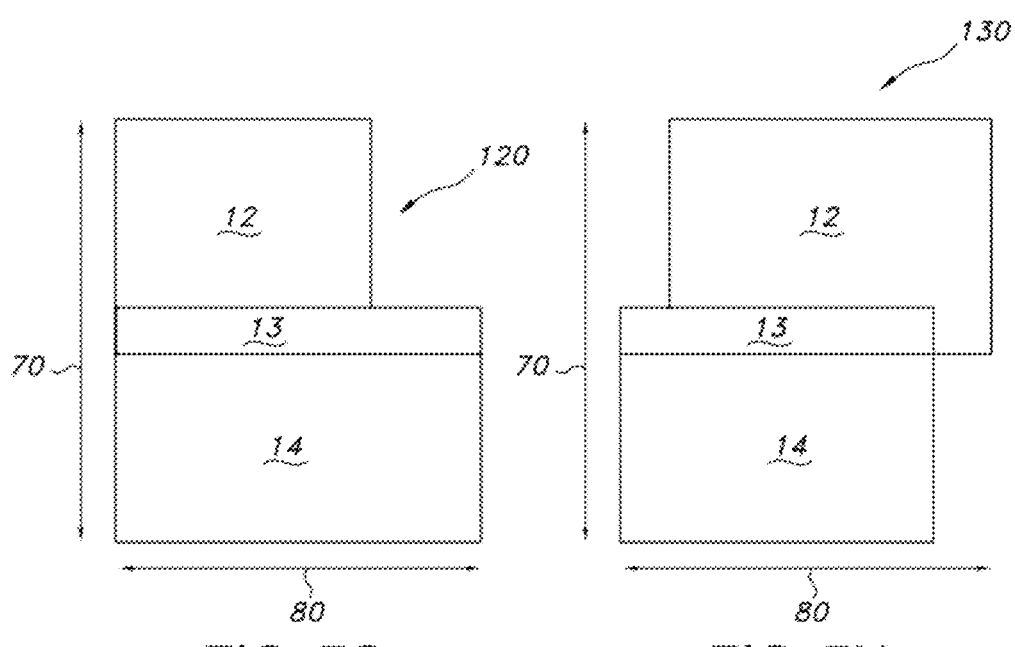

TAMPON HAVING MULTIPLE ABSORBENT REGIONS

PRIORITY

This non-provisional application claims priority of Provisional Application No. 61/482883, filed on May 5, 2011. The entirety of Application No. 61/482883 is incorporated herein by reference.

FIELD OF INVENTION

The present invention concerns personal hygiene products, more particularly, body cavity inserts such as catamenial tampons, and the absorbent structures used in such inserts and tampons.

BACKGROUND OF THE INVENTION

There are two basic types of catamenial tampons used for feminine hygiene currently available on the market, each of which are ideally designed to offer discreet and comfortable protection. The first type is a digital tampon which is designed as an absorbent structure to be inserted into a body cavity such as a woman's vagina, directly by a user's fingers. The second type is a tampon which is designed to be inserted with the aid of a separate applicator. Such applicators are typically manufactured of either paperboard or polymer materials. Both types of tampons can be made by folding or rolling a loosely associated strip or ribbon of absorbent material into an elongated or other shape, such as a "W", "V" or cup-like shape, often referred to as a "blank" or "softwind," in the case of a rolled ribbon. Such is described in U.S. Pat. No. 5,533,990 to Yeo. The softwind is then, in one configuration, either radially and/or biaxially compressed to form the processed tampon absorbent. A description of a method for making a radially wound absorbent is disclosed in U.S. Pat. No. 4,816,100 to Friese. The radial wound softwind may be compressed into a compacted absorbent like that disclosed in U.S. Pat. No. 6,310,269 to Friese.

A compressed absorbent structure is also known in the patent art as a "pledget". In alternative tampon pledget designs, such as those described in U.S. Pat. No. 6,837,882, and US20080132868 to Jorgensen, the pledget is formed into a chevron-shaped structure and then compressed, or a perpendicularly overlapping layer configuration and then compressed/molded into a cup-like shape. Suitable methods for making "W"-folded pledgets or "V"-folded pledgets are disclosed in U.S. Pat. No. 6,740,070 to Agyapong; U.S. Pat. No. 7,677,189 to Kondo; and U.S. 2010/0114054 to Mueller. Each of the foregoing patents is hereby incorporated by reference in its entirety.

Each of the above described pledgets may or may not include a cover which will facilitate holding the absorbent material together once compressed. In both types of tampons (the digital or applicator), a withdrawal string is typically attached to the absorbent, either before or after compression, to facilitate removal of the tampon or insert from the user's vagina or other orifice, after it has absorbed a certain quantity of body fluid, such as urine, menses, blood, etc. The withdrawal string may be physically attached to the absorbent either through a bonding method, such as stitching, thermal, adhesive or other mechanical means, or alternatively, rather than being physically attached, it may be merely wrapped around the absorbent or a portion thereof, during the manufacturing process, and allowed to hang off of one end of the finished tampon absorbent (sometimes referred to as tampon "blank").

As the various tampons described above are saturated by menses, they expand into a variety of shapes, depending on the initial tampon structure. It has been found that many of these differently shaped tampons, both digital as well as those delivered by an applicator, are often unable to prevent premature leakage of body fluid, that is leakage of menses from a user's vagina prior to the complete saturation of the tampon absorbent. Premature leakage, which often results from an inefficient use of tampon absorbent capacity, can result from a number of factors. For example, one factor is the tampon does not properly fit above the introital region of the vagina.

Another factor is that the tampon is not shaped correctly to intercept fluid flow through the vaginal canal. Still another factor is that the folds and convolutions of the vagina are not all in contact with the tampon absorbent and therefore body fluid is able to bypass the tampon. Still, a further reason for leakage lies in the absorbent fiber or layer construction of the tampon, such that the tampon design itself inadvertently interferes with maximum menses absorption. Yet a further factor is the residual menses which accumulates on the withdrawal end of a tampon during the withdrawal process and which exits the vagina at the onset of the tampon removal. Therefore, even if a tampon is shaped to prevent leakage in use, it has been found that leakage may still occur upon tampon absorbent withdrawal.

Further, since insertion stresses on a tampon absorbent may be different depending on whether a tampon absorbent is a digital or applicator-type tampon, there is a need for a tampon absorbent structure which can provide leakage protection for a variety of tampon formats. There is a need for a tampon absorbent which can provide the strength necessary to accommodate digital and applicator insertion and yet still allow for leakage protection.

It has also been found that tampon absorbents may not provide predictable comfort during use or withdrawal, as a result of their various expansion shapes over time. For example, tampon absorbents made from a single ribbon material or substantially overlapping sheet materials, have been found to sometimes result in inadequate customized fit. Even when such single ribbon tampon absorbents or substantially overlapped sheet materials are shaped and otherwise mechanically manipulated, they have also sometimes resulted in inadequate customized fluid handling and fit.

Patent literature in the tampon field has explored the use of different expansion restricting elements in a tampon absorbent design. For instance, various techniques have been described for creating different expansion shapes for digital tampon components. For example, various restrictive elements have been used to wrap the withdrawal end of a tampon absorbent so as to limit expansion of the tampon in this region. The literature has suggested that by maintaining a smaller diameter withdrawal end following use, such tampons could more easily be removed from the vaginal canal, causing less discomfort to the user. See for example, the restrictive elements in U.S. Pat. No. 2,330,257 to Bailey; U.S. Pat. No. 3,038,214 Griswold et al.; and JP 2004-097304, EP 1481656, and EP 2184044. Some of the restrictive elements described include threads, rings or moisture impermeable overwrap materials which completely and tightly overwrap the withdrawal end of a tampon absorbent. Some of the hydrophobic or liquid impermeable overwraps described are also designed to form a cap on the withdrawal end, thereby limiting leakage during tampon absorbent removal. A further example of an overwrap may be found in WO2005/048901. Other methods for creating restrictive regions include the use of hydrophobic injectable materials, which limit the amount of menses that can be absorbed in particular areas of the tampon absorbent. For example, restrictive expansion using compositions impregnated into portions of the tampon structure is described in U.S. 2008/0154222 to Chaffringeon. The use of specific segmented grooves, voids or discontinuities along a tampon length to encourage fluid handling differences or absorbent channel enhancements at various regions of a tampon is described in U.S. 20110092940 to Fung et al. See also in this regard, U.S. 20080262463 to Noel et al. Even with such diverse designs for tampon restriction elements, there is still a need for tampon absorbents which provide for more efficient usage of their entire structure.

Some patent references also describe the use of various bending-influencing features along a tampon length such as in U.S. Pat. No. 2,858,831 to Graham, Jr. Such features include fiber orientation and disk segmentation/discontinuities. Even with such bending features, there is still a need for improved comfort of tampon absorbents.

While various types of absorbent enhancement structures or restrictive structures have been described in the foregoing references, these references focus on use of either single ribbon structures or overwrapping absorbent layered structures in which absorbent sheets are substantially positioned one on top of the other along the entire tampon length, such that the type(s) of absorbent along the finished length of a tampon absorbent (facing the vaginal canal) is essentially the same along the entire length dimension, the exception being tampon absorbents with topographical patches (or islands) of different materials. Essentially, such tampon absorbents demonstrate similar absorbency functionality along their entire length and are formed via bonding in the longitudinal direction of the tampon. In addition to functional disadvantages of such structures, the manufacturing processes for creating such structures pose layer registration challenges.

There remains a need for a tampon and tampon absorbent product that prevents leakage of body fluid soon after being inserted into a woman's vagina, provides efficient utilization of the entire absorbent structure during use, without the necessary use of blocking agents or extraneous chemistry, or physical structures, and which also provides for comfort to a user throughout various daily activities.

SUMMARY OF THE INVENTION

A tampon absorbent for insertion into a vaginal cavity is provided. The tampon absorbent includes a longitudinal direction and has an insertion end and a withdrawal end. The tampon absorbent includes a first absorbent material portion at the insertion end for capturing body fluid and demonstrating a first expansion capacity, and a second absorbent material portion at the withdrawal end for storing body fluid and demonstrating a second expansion capacity. The second absorbent material portion is partially wrapped around the first absorbent material portion in a direction transverse to the longitudinal direction, at a bonding region, whereby the first absorbent material portion is bonded to the second absorbent material portion at the bonding region.

In another embodiment of the invention, a tampon for insertion into a vaginal cavity is provided which includes a tampon absorbent. The tampon absorbent has a longitudinal direction including an insertion end and a withdrawal end. The tampon absorbent further includes a first absorbent material portion at the insertion end for capturing body fluid and demonstrating a first expansion capacity, and a second absorbent material portion at the withdrawal end for storing body fluid and demonstrating a second expansion capacity. The second absorbent material portion partially wraps around the first absorbent material portion outer surface at a bonding region. The first absorbent material portion is bonded to the second absorbent material portion at the bonding region, and a withdrawal string is looped around the tampon absorbent.

In a further alternative embodiment of the invention a method of manufacturing a tampon absorbent is provided that includes the steps of 1) providing one each of a ribbon of a first absorbent material and a second absorbent material, each of said ribbons having a longitudinal direction, 2) positioning the second absorbent material ribbon such that one of its edges is juxtaposed over the edge of the first absorbent material ribbon, thereby forming an overlap of the two ribbons in a direction transverse to the longitudinal direction of the ribbons, 3) folding the second absorbent material ribbon around the edge of the ribbon of the first absorbent material, by means of a folding plate, 4) bonding the first absorbent material ribbon to the second absorbent material ribbon at the overlap of the ribbons thereby forming a bonding region.

In still a further embodiment of the invention a method of manufacturing a tampon is provided that includes the steps of 1) providing a ribbon of a first absorbent material and a second absorbent material, each having a longitudinal direction and transverse direction, 2) positioning the second absorbent material ribbon such that one of its edges sits over the edge of the first absorbent material ribbon in a direction transverse to the longitudinal direction of each of the ribbons, thereby forming an overlap of the two ribbons, 3) folding the second absorbent material ribbon around the edge of the ribbon of the first absorbent material, preferably by means of a folding plate, 4) bonding the first absorbent material ribbon to the second absorbent material ribbon at the overlap thereby forming a bonding region, 5) rolling the bonded absorbent material ribbons of step, 4) about an axis that is located parallel to the longitudinal direction of the bonded ribbons to form a tampon blank, 6) inserting the tampon blank in a tampon pressing section of a press for manufacturing a tampon, 7) pressing essentially radially the tampon blank in the press to form a tampon.

In still a further embodiment, a tampon absorbent for insertion into a vaginal cavity has a longitudinal direction including an insertion end and a withdrawal end. The tampon absorbent includes a first absorbent region at the insertion end for storing body fluid and demonstrating a first expansion capacity. A second absorbent region is at the withdrawal end for storing body fluid and demonstrating a second expansion capacity. A third absorbent region is situated between the first absorbent region and the second absorbent regions in the longitudinal direction, wherein the first absorbent region is bonded to the second absorbent region at the third absorbent region.

In still a further embodiment, a tampon absorbent for insertion into a vaginal cavity has a longitudinal direction including an insertion end and a withdrawal end, and a transverse direction. The tampon absorbent includes a first absorbent region at the insertion end for storing body fluid and demonstrating a first expansion capacity. A second absorbent region is at the withdrawal end for storing body fluid and demonstrating a second expansion capacity. A third absorbent region is situated between the first absorbent region and the second absorbent regions in the longitudinal direction, wherein the first absorbent region is bonded to the second absorbent region in the transverse direction, at the third absorbent region.

In still a further embodiment, the absorbent material portions are of different colors. In still a further alternative embodiment, a first absorbent material portion is of a first color, a second absorbent material portion is of a second color, and a bonding region, bonding the two absorbent material portions together is of a third color, which is a blending of the first and second colors. In still a further embodiment, colors of absorbent material portions can be seen through coversheets on tampon absorbents. Each of the absorbent regions preferably demonstrates different absorbency characteristics, including expansion capacity, stiffness and density. This three-absorbent-region structure, with transverse directional bonding, provides unique performance characteristics in three separate locations along the tampon absorbent length.

Therefore in one aspect, such tampon absorbent provides for two absorbent material portions along the tampon absorbent longitudinal direction. Such two absorbent material portions allow for a more moisture sensitive portion (having greater expansion capacity) towards a tampon absorbent insertion end, and a less moisture sensitive portion (having lower expansion capacity) towards a tampon absorbent withdrawal end. By bonding the two absorbent material portions in a direction transverse to the longitudinal direction, a bonding region creating a hinge or flex point is created, thereby allowing the two portions to bend with respect to each other (along the longitudinal direction), providing for comfort in use. Use of different moisture sensitive portions allows for the tampon absorbent to physically accommodate the sometimes non-cylindrical aspects of a vaginal canal. Such allows for the comfortable insertion (with sufficient columnar strength) of the tampon absorbent, as well as its comfortable withdrawal, while still providing shape conforming attributes to reduce leakage.

BRIEF DESCRIPTION OF THE DRAWINGS

FIG. 1 shows a side perspective view of a process-finished tampon containing a tampon absorbent of the present invention, with the tampon in an initial unused state.

FIG. 2 shows a side perspective view of the tampon of FIG. 1 demonstrating the expansion characteristics of the tampon during use inside a user's vaginal canal.

FIG. 3 shows a side perspective view of the tampon of FIG. 1, demonstrating the ability of the tampon to flex and bend around a particular tampon bonding region, during use.

FIG. 5A shows a perspective view of a portion of an alternate embodiment of the two-ribbon, bonded absorbent composite of FIG. 5, prior to the composite being formed into a softwind (and tampon absorbent).

FIG. 6 shows a cross-section view of a portion of a rolled softwind made from a two-ribbon bonded absorbent composite of the present invention (such a softwind being shown in FIG. 9 at 147).

FIG. 7A shows a cross-section view of an alternate embodiment of a portion of a rolled softwind made from a two-ribbon bonded absorbent composite of the present invention (such a softwind being shown in FIG. 9 at 147).

FIG. 7G shows a partial top view of an alternate embodiment of the two-ribbon bonded absorbent composite of FIG. 4.

FIG. 7H shows a partial top view of an alternate embodiment of the two-ribbon bonded absorbent composite of FIG. 4.

DEFINITIONS

Figure 4:
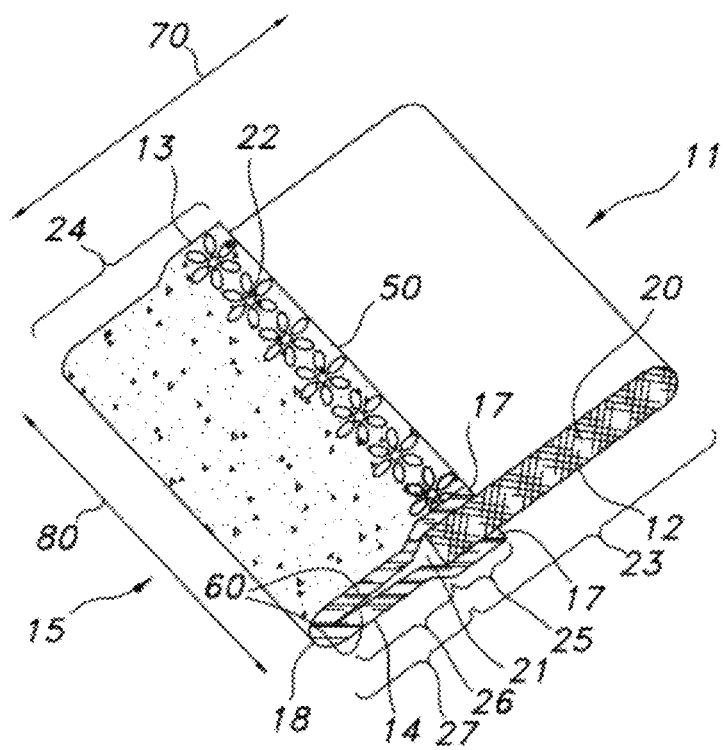
FIG. 4 shows a perspective view of a portion of a two-ribbon, bonded absorbent composite, which makes up the tampon absorbent, prior to the composite being rolled into a softwind (and tampon absorbent).

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, "disposable" means being disposed of after a single use and not intended to be washed and reused.

As used herein, the term "autogenous bonding", "autogenously bondable" and similar forms of these words, means bonding provided by fusion and/or self-adhesion of fibers and/or filaments without an applied external adhesive or bonding agent. Autogenous bonding can be provided by contact between fibers and/or filaments while at least a portion of the fibers and/or filaments are semi-molten or tacky. Autogenous bonding may also be provided by blending a tackifying resin with the thermoplastic polymers used to form the fibers and/or filaments. Fibers and/or filaments formed from such a blend can be adapted to self-bond with or without the application of pressure and/or heat. Solvents may also be used to cause fusion of fibers and filaments which remain after the solvent is removed.

As used herein, the term "cross-section", "cross-sectional" and similar forms of these words, mean the plane which extends laterally through the tampon and which is orthogonal to the longitudinal axis of the tampon or tampon absorbent.

For the purposes of this application, the term "tampon" shall refer to the "tampon absorbent" structure and the additional structures associated with the tampon absorbent structure, such as the withdrawal string and applicator, as the case may be. The term "tampon absorbent" shall refer to an absorbent composite made from ribbons, pledgets or softwinds, and cover, if present. The absorbent composite will desirably in one embodiment, be formed of two ribbons in a bonded absorbent composite. A "processed-finished" tampon shall be synonymous with a tampon, and is meant to emphasize that a tampon illustrated is at a stage in which manufacturing steps are completed and it is ready for use.

For the purposes of this application, tampons, tampon absorbents, bonded absorbent composites, pledgets, and absorbent ribbon materials making up bonded absorbent composites will be described as having "insertion" ends and "withdrawal" ends. The term "insertion" end will refer to that end of the tampon, tampon absorbent, pledget or absorbent ribbon material which is initially inserted into a user's vagina. The term "withdrawal" end, shall refer to that end of the tampon, tampon absorbent or absorbent ribbon material which is initially withdrawn from a user's vagina and which may be accompanied by a withdrawal string (in the case of a tampon). The tampons, tampon absorbents, pledgets and absorbent ribbon materials described herein shall each have a longitudinal direction and a transverse direction or width direction (which is perpendicular to the longitudinal direction (axis). Upon the rolling and compression of bonded absorbent ribbons/tampon absorbents of the present invention, the longitudinal direction of the ribbons/pledgets shall become the longitudinal direction of the tampon. It should be noted, that while rolled and compressed tampon absorbents are but one embodiment of the invention, the invention also contemplates use of the alternative pledget structures as described above.

As used herein, the term "diameter" and similar forms of this word, means the cross-sectional diameter of the tampon.

As used herein the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

Repeat use of reference characters in the present specification and drawings is intended to represent same or analogous features or elements of the invention. It should also be recognized that elements of one embodiment may be placed in other embodiments, unless otherwise stated.

DETAILED DESCRIPTION OF THE INVENTION

The disposable tampon and tampon absorbent (made from bonded absorbent composites) of the present invention, are designed to be inserted above the introital region of a woman's vagina, desirably above the pelvic floor muscles, and are designed to function so as to intercept the fluid flow of menses, blood, and other body fluids and prevent the fluid from exiting the vagina, or other body cavity. The tampon absorbent of the present invention is prepared from at least two different absorbent material portions (desirably from two different absorbent ribbons), which together form a unified bonded absorbent composite via a bonding region. To obtain a better understanding of the absorbent material portions used to prepare the tampon absorbent of the present invention, attention is directed to the figures.

Figure 9:
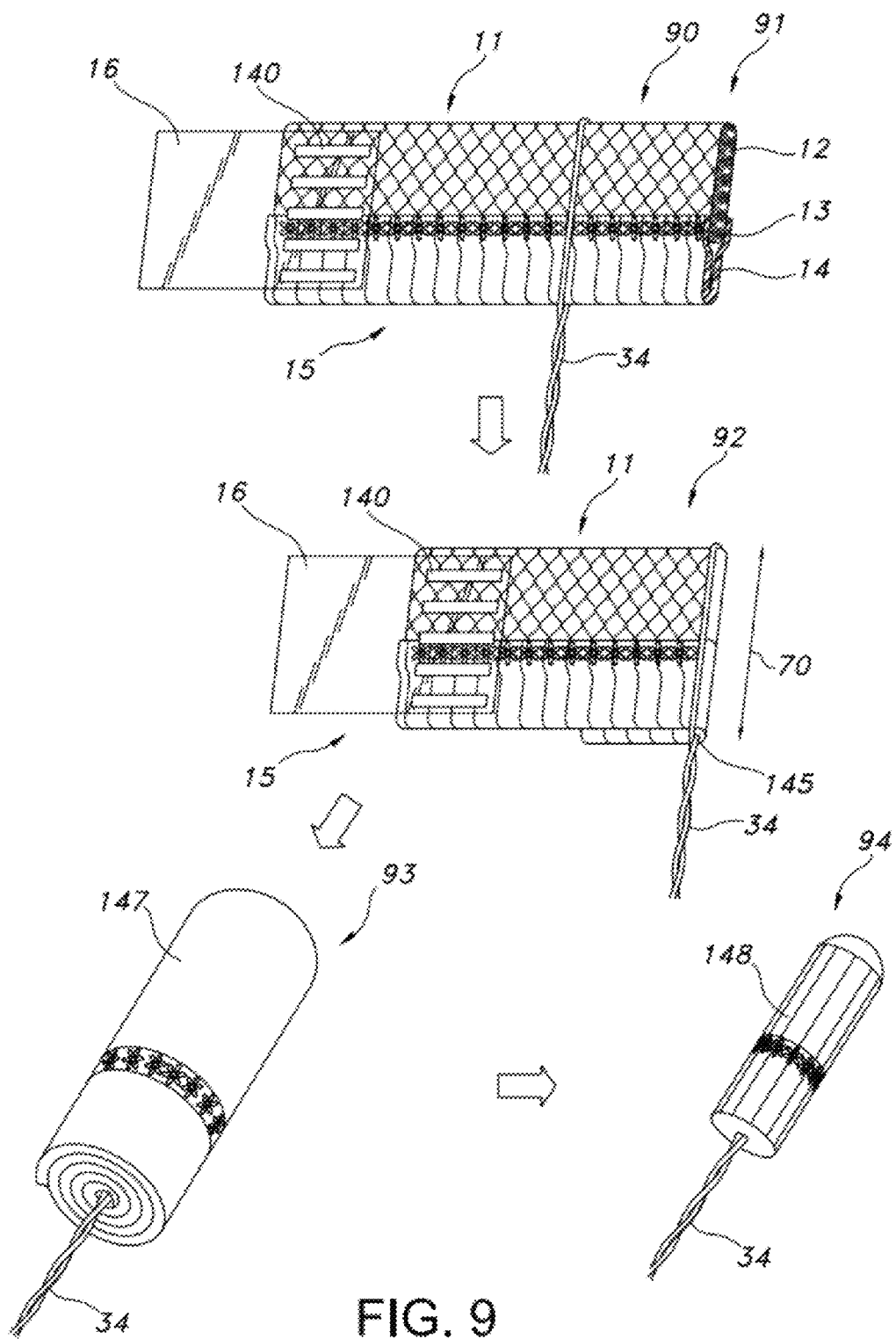
FIG. 9 shows a flow chart of a tampon manufacturing process using a tampon absorbent of the present invention.

As is shown in FIG. 1, in one embodiment the tampon 10 of the current invention includes a tampon absorbent 90 that has been rolled into a softwind and then compressed into the generally cylindrical shape as shown, and having an insertion end 11 and a withdrawal end 15. In this figure, the tampon 10, also includes a cover sheet layer 16, which does not completely cover the entire tampon absorbent 90, and a withdrawal string 34. As can be seen in the figure, the cover sheet 16 does not cover the rounded tip of the tampon at the insertion end, but does extend in the direction of, or to the withdrawal end. It is contemplated that the cover sheet in certain embodiments, may also extend to cover the entire insertion end, or alternatively extend beyond the withdrawal end to form a tampon skirt (not shown), which hangs from the withdrawal end 15. The tampon absorbent generally includes a first absorbent portion 12, made of a first absorbent material and located towards the insertion end 11, and a second absorbent portion 14, made from a second absorbent material, and located towards the withdrawal end 15. The tampon (and necessarily the tampon absorbent, bonded absorbent composite and ribbons) each include a longitudinal direction (axis) 70 and transverse direction (axis) 80 perpendicular to the longitudinal direction (as clearly see in FIG. 4). The withdrawal string 34 (as also seen in FIG. 9) is in one embodiment, looped around the tampon absorbent 90 and hangs from the withdrawal end 15 of the tampon 10. A transverse directional bonding region 13 attaches the first absorbent material portion 12 to the second absorbent material portion 14. The bonding region essentially connects the bonded absorbent composite.

Figure 5:
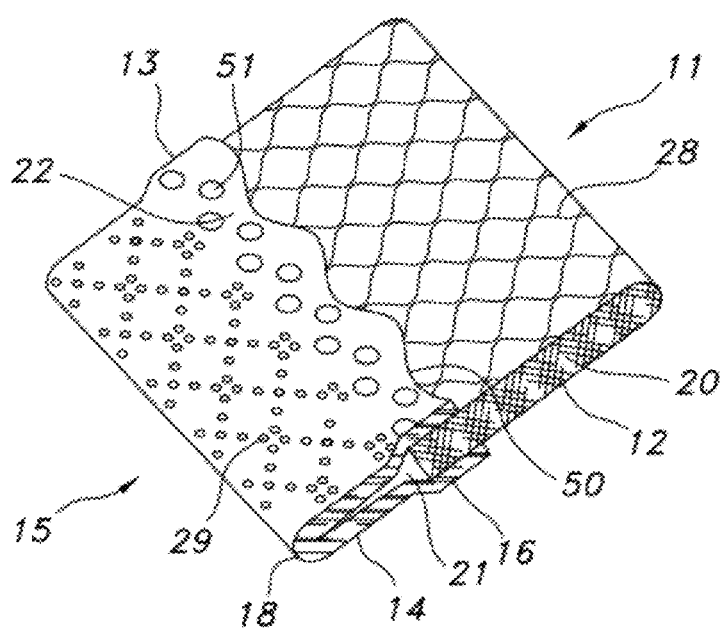
FIG. 5 shows a perspective view of a portion of an alternate embodiment of the two-ribbon, bonded absorbent composite of FIG. 4, prior to the composite being formed into a softwind (and tampon absorbent).

The transverse directional bonding region 13 is desirably formed using only pressure. For example, a pressure of between about 2000 (53PSI/3.7 Bar) and 2500 lbs. (65 PSI/4.5 Bar) of force (8896-11,121 N) may be used between two cylindrical bonding rolls (anvil and pattern rolls) to bond the first absorbent material portion to the second absorbent material portion. Alternatively, heat and pressure can be used to bond the absorbent portions. Still in a further embodiment, individually or collectively, heat, pressure, adhesive, ultrasonic, mechanical entanglement or other autogenous bonding techniques may be used to connect the two absorbent portions. The bonding region 13 may include any number of bond pattern elements, although a series of flowers 22 are shown in the embodiment of FIG. 1. Other potential bond element designs include staggered dots or dashes as seen in FIGS. 5 and 5A, curved bond lines, or a combination of abstract, geometrical or realistic bond shapes and objects. As shown, the tampon 10 also desirably includes recessed grooves 19 configured along its longitudinal direction (or axis) 70, and created by traditional radial/or biaxial tampon compression equipment. The cover sheet layer 16 may in one embodiment, be translucent or semi-translucent, to allow for the observation of internal absorbent layers (as seen in the figure as allowing the colored second absorbent material portion to be seen), or may be opaque so as to help mask staining in the tampon internal layers. The cover layer optionally does not completely envelop the absorbent composite as can be seen in the figure, but can cover all outer surfaces if desired. In an initial stage, as would be seen by a consumer prior to use, a processed-finished tampon would include a generally cylindrical shape with uniform diameter X1 along its longitudinal direction 70, except for the insertion end 11, which desirably tapers to a rounded, cone-shaped, hemispherical or parabolic shaped tip. In one embodiment, as illustrated in FIG. 1, the second absorbent material portion 14 can be of a different color or appearance than the first absorbent material portion 12, as can be seen through the translucent cover layer 16.

As can be seen in FIG. 2, while in use, the tampon 10 of the present invention is designed to be positioned within a woman's vagina 19, desirably above the pelvic floor muscles, so as to conform to the non-straight line of the vaginal canal. During use, the first absorbent material portion 12 demonstrates a first expansion and the second absorbent material portion 14 demonstrates a second expansion, with the first expansion often being significantly larger than that of the second expansion. In one embodiment, the bonding region 13 demonstrates a different expansion capacity, density and absorbency from each of the first and second absorbent material portions.

It is possible for the second absorbent material portion 14 to expand prior to the first absorbent material portion 12. The expansion of the second absorbent is not necessarily dependent on the expansion of the first absorbent, and it can open outwardly, independently. In one embodiment, the expansion of the first absorbent material portion 12 can increase under free swell conditions (without any containment walls surrounding the tampon) by approximately 233% or less. For example, the diameter of the first absorbent material portion 12, excluding the rounded tip, can expand from approximately 12 mm to 28 mm, when measured at its widest point. The expansion of the second absorbent material portion 14 is often slight X2 with respect to the tampon second absorbent material portion original compressed diameter X1. In any event, the first absorbent material portion 12 will normally expand to a larger final diameter than the second absorbent material portion 14. In one embodiment, the ratio of diameter expansion, excluding the rounded tip at the insertion end, between the first absorbent material portion 12 (at its widest point in the transverse direction) and the second absorbent material portion 14, at its widest point in the transverse direction, is between about 1:0.9 to 1:0.5. In a second embodiment, the ratio of expansion between these two portions is about 1:0.75. In one embodiment, the tampon 10 demonstrates an absorbent capacity of less than 6 g as measured by the Syngenta test method of Edana from 350.0-02 (February 2). In other alternative embodiments, the tampon 10 demonstrates an absorbent capacity of between 6 and 9 g, between 9 and 12 g, between 12 and 15 g, or between 15 and 18 g.

While in use, the tampon demonstrates the ability to flex and bend along a flex line above the bonding region 13 (at a position along the first absorbent material portion 12 towards the insertion end), so as to provide comfort to a user during daily activities and to conform to the non-straight vaginal canal if need be. This flexing is illustrated in FIG. 3, where the first absorbent material portion 12 is shown in a bent position with respect to the longitudinal direction 70 (axis) of the tampon 10. The tampon retains a narrower diameter in the second absorbent material portion at the withdrawal end 15 so as to facilitate easy removal. The tampon 10 demonstrates a columnar strength to allow for comfortable insertion and removal.

The tampon absorbent 90 (and tampon 10) of the contemplated invention therefore includes three distinct absorbent regions along its longitudinal direction 70. The first region is made up of the first absorbent material portion 12, the second region is made up of the bonding region 13 (with the bonding occurring in the transverse direction of the tampon absorbent/tampon), which includes an overlap of the first absorbent material portion 12 and the second absorbent material portion 14, and a third region, which includes only the second absorbent material portion 14. Each of these three regions demonstrates different absorbent capacities and properties, such as expansion capacity and density. Each of these regions provide absorbent capacity, while still providing in a unified design, the ability (of the tampon) to flex during user movement and restricted withdrawal end-expansion to allow for comfortable removal. Essentially, along the longitudinal direction of the tampon absorbent and tampon 70 produced therefrom, there are three distinct absorbent regions, having different properties and comprised of three different material configurations.

As noted, FIG. 4 illustrates a perspective view of the two-ribbon, bonded tampon absorbent composite of FIG. 1, prior to rolling into a softwind and compression into a processed-finished tampon absorbent, cylindrical configuration. The bonded absorbent composite is essentially shown in a flattened state. As can be seen in this figure, the first absorbent material portion 12 sits within a partial "Y" configuration formed from the second absorbent material portion 14. Desirably, in one embodiment, a hollow space or cavity 21 is positioned adjacent the first absorbent 12 towards the withdrawal end 15. Desirably the first absorbent material portion 12 is a single layer 20, such as a carded web material, and the second absorbent material portion 14 is a single layer 18 that partially wraps around a portion of the first absorbent material portion 12 at areas 17. The second absorbent material portion 14 at the withdrawal end 15, forms the cavity 21 between two segments of the folded layer 18, as a result of the manufacturing process. Alternatively during the manufacturing and subsequent compression process, the second absorbent material portion 14 may be tightly folded so that it closely aligns to the lower withdrawal end edge of the first absorbent material portion 12, and in fact touches it, such that there is no cavity present, but still there is a lower second absorbent material portion 14 that hangs from the first absorbent material portion 12 without overlapping it. This can be seen for example in FIG. 7D. Desirably the second absorbent material portion 14 is a bonded carded web. As shown in FIG. 4, the second absorbent material portion 14 can be a continuous single layer that wraps around one edge of the first absorbent material portion 12 in a direction transverse to the longitudinal direction of the tampon absorbent. A section of the folded second absorbent 14 does not overlap with the first absorbent material portion 12 along the longitudinal direction 70, but instead hangs adjacent to it (along length 27) forming the withdrawal end 15 of the tampon absorbent. The second absorbent portion 14 is bonded to the first absorbent portion 12 in the bonding region 13, shown in this figure through the use of a floral bonding pattern 22. This bonding occurs at the surfaces of the first absorbent material portion 12 and the inwardly directed surfaces of the second absorbent material portion 14.

In one embodiment, the size of the first absorbent 12 along the longitudinal direction 23 (as measured from the tip at the first absorbent material portion insertion end 11, to the tip near the first absorbent material portion 12 withdrawal end 15, is between about 15 and 50 mm. In a second embodiment, the size of the first absorbent 12 in the longitudinal direction is between about 40 and 45 mm. Given the overlap of the first absorbent material portion 12, by the second absorbent material portion 14, it is likely that only about 30 mm of the first absorbent material portion 12 would be visible from the outside of the tampon 10. In a further embodiment, the size of one of the side layers 60 of the second absorbent material portion 14 in the longitudinal direction 24 as measured from the bonding region 13 exposed edge 50 to the second absorbent material portion withdrawal end 15 edge, is between about 5 and 35 mm. In still a further embodiment, the size of one of the side layers of the second absorbent material portion 14 in the longitudinal direction 24 is between about 20 and 25 mm. Desirably, the size of the bonding region 13 in the longitudinal direction 25 is between about 3 and 35 mm. More desirably, the size of the bonding region 13 in the longitudinal direction 25 is between about 7 and 15 mm. The bonding region 13 helps to create a flexing zone just above it in the longitudinal direction, in the direction of the insertion end 11, which provides a hinge point in the tampon and tampon absorbent. With the second absorbent material portion 14 not expanding to the extent of the first absorbent material portion 12, and the two absorbent material portions protruding from both sides of the flexing zone, a hinge point is created.

The size of the cavity 21 (if present, typically in the softwind state of the tampon absorbent) in the longitudinal direction 26 adjacent the first absorbent material portion end 12, and formed from the two side layers 60 of the second absorbent material portion end 14, is between about 0 and 40 mm, in one embodiment. In a second embodiment the size of this cavity 21 if present in the softwind in the longitudinal direction, is between about 5 and 20 mm. More desirably, the size of the cavity 21 if present in the softwind in the longitudinal direction 26, is between about 5 and 13 mm. The cavity 21 is typically not present in the compressed state of the tampon absorbent, but is theorized to reopen upon expansion/absorption of body fluids.

Figure 7B:
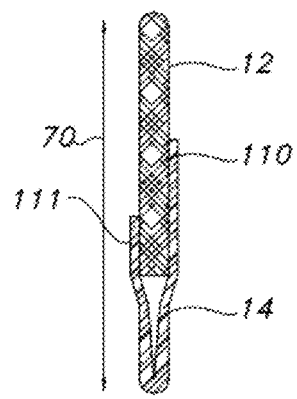
FIG. 7B shows a cross-section view of an alternate embodiment of a portion of a rolled softwind made from a two-ribbon bonded absorbent composite of the present invention (such a softwind being shown in FIG. 9 at 147).
Figure 7C:
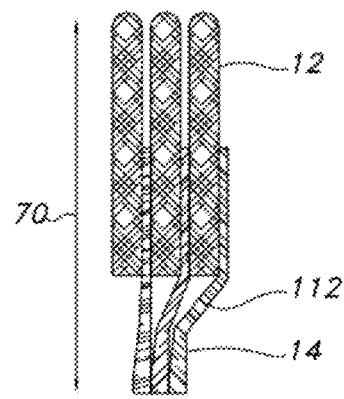
FIG. 7C shows a cross-section view of an alternate embodiment of a portion of a rolled softwind made from a two-ribbon bonded absorbent composite of the present invention (such a softwind being shown in FIG. 9 at 147).
Figure 7D:
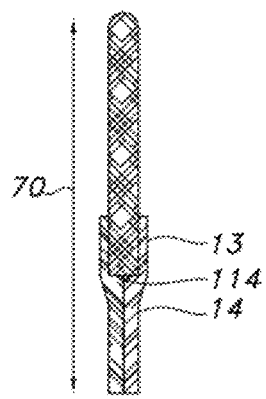
FIG. 7D shows a cross-section view of an alternate embodiment of a portion of a rolled softwind made from a two-ribbon bonded absorbent composite of the present invention (such a softwind being shown in FIG. 9 at 147).

As indicated, in one embodiment following manufacture, the tampon absorbent and tampon produced therefrom does not include a cavity, but instead has the second absorbent in contact with the first absorbent in place of the cavity (as seen in FIG. 7D at 114). In one embodiment, the size of the side layers 60 of the second absorbent 14 that are not overlapping with the first absorbent material portion 12 at the bonding region 13 is between 3 and 40 mm in the longitudinal direction 27. Alternatively, their size in the longitudinal direction 27 is between about 5 and 20 mm. Desirably the degree of overlap between the first absorbent material portion 12 and second absorbent material portion 14 in the longitudinal direction (at the bonding region) is between 5 and 70% of the total length of the tampon absorbent 90 in the longitudinal direction (the sum of 23 and 27). The cavity 21 is desirably present in the proposed softwind of a ribbon-based, bonded absorbent composite to capture fluid during use.

As can be seen in FIG. 4, the second absorbent material portion 14 may include a colorant (shown with shading) in order to distinguish the two absorbent portions. In such a case, the different functionality of the two portions is highlighted for the user. If colorant is used in the second absorbent material portion 14, it is desirable in one embodiment for the ratio of colored second absorbent material portion to non-colored first absorbent material portion visible on the tampon surface, to be between 90%/10% and 10%/90%. In another embodiment, it is desirable for the visible ratio of the second absorbent material portion to first absorbent material portion be about 40%/60%. In a further alternative embodiment (not shown), each of the first and second absorbent material portions would include a different colorant. In this embodiment, the differently colored layers would overlap at the bonding region 13 thereby producing a third color in the bonding region as a result of the overlap. For example, should the first absorbent be colored yellow and the second absorbent be colored blue, the bonding region would take on a green color to an observer as a result of the observer's brain blending the yellow with blue through observation. This three layer color arrangement could be used to provide a message to the consumer as to the three different absorbent regions along the tampon's longitudinal direction 70. Bonding of two colored regions in a bonding region to achieve a third colored region at the bonding region, can be accomplished using thermal bonding, autogeneous bonding, ultrasonic bonding and adhesive bonding.

As can be seen in FIG. 5, in an alternative embodiment of the ribbon-based, bonded absorbent composite of FIG. 4, the first absorbent material portion 12 is compressed prior to manufacture into the absorbent composite, with a compression pattern, such as with a wave pattern 28, hexagonal pattern, or honeycombed pattern (not shown). Any number of known absorbent compression patterns are envisioned in order to help create a more cohesive overall absorbent structure. Additionally, the second absorbent material portion 14 may also be compressed, such as with an overall diamond-configured dot embossing pattern 29. Such wave and diamond patterns can increase the cohesiveness of the overall tampon absorbent, and therefore the tampon. The bonding region 13 may include an exposed edge 50 that is not straight, such as a scalloped, zigzag, wavy, or other curvilinear edge design rather than the straight exposed edge illustrated in FIG. 4. Alternate bonding patterns, such as an alternating dot pattern 51 may be used in the bonding region 13. Still, in a further alternative embodiment, as seen in FIG. 5A, staggered bonding dot patterns, such as a series of four staggered dots 52 and two staggered dots 53 may be employed. Desirably the bond surface area of the bonding patterns in the bonding region 13 is between about 5 and 100% (100% in the case of smooth bond rolls). In an alternative embodiment, the bond surface area of the bonding patterns in the bonding region 13 is between about 5 and 70%. Still in a further alternative embodiment, the bond surface area of the bonding patterns is between about 5 and 25% of the bonding region 13 surface area. In one embodiment, the bonding pattern includes dot patterns having a 1-2 mm dot diameter. In another embodiment, the bonding region length 25 in the longitudinal direction, is about 5 mm. The bonding region surface area is considered to be the regions of overlap 17 between the second absorbent material portion 14 and the first absorbent material portion 12 in the longitudinal direction shown at 25.

As can be seen in FIG. 6, a stylized partial cross-section view of a softwind 147 made from the two-ribbon based, bonded absorbent composite (in the longitudinal direction) of FIG. 9 is shown. Cover 16 partially envelopes the outer edges of the first and second absorbent material portions 12 and 14. The folds or lobes of the two-ribbons (first absorbent material portion 12 and second absorbent material portion 14) are separated by spaces in the softwind, which when compressed in the processed-finished tampon are not readily apparent. Additionally, although not shown, spaces adjacent bonding regions 13 are also present between lobes in the softwind. As the compressed tampon absorbent is put in use, and expands as a result of fluid absorption, the spaces between the lobes and bond regions, as well as cavities, re-emerge in the structure to capture body fluid.

As can be seen in FIG. 7A, which illustrates a cross-section view of an alternative embodiment of a softwind 147, rather than having the side layers 60 of the second absorbent material portion 14 be of a continuous layer that wraps around the withdrawal end edge of the first absorbent material portion 12 (as shown in FIGS. 4, 5 and 6), two discontinuous layers 61 of second absorbent portion 14 materials, meet from each side of the first absorbent material portion 12, at the withdrawal end 15 (forming the "Y" bottom) of the first absorbent layer 12.

As can be seen in FIG. 7B, in a further alternate embodiment, as shown in cross-section, the second absorbent material portion 14 may be folded around the edge of the first absorbent material portion 12, such that the longitudinally directed overlapping portions 110 and 111 of the second absorbent material portion 14, are not symmetrical on opposite facing side edges of the first absorbent material portion.

As can be seen in FIG. 7C, in a further alternate embodiment of a softwind 147 portion shown in cross-section, the second absorbent material portion 14 may be positioned along only one side edge 112 of the first absorbent material portion 12 in the longitudinal direction 70, such that the "Y" shaped configuration is only formed upon rolling and compression of the bonded absorbent composite.

As can be seen in FIG. 7D, in a further alternate embodiment, shown in cross-section, the second absorbent material portion 14 may be positioned close to the first absorbent material portion in the bonded absorbent composite. In this alternate structure, the location on the bonded absorbent composite that was previously described as including a cavity 114, either does not include a cavity or includes one that is barely present in the softwind, and further reduced or eliminated in its entirety during later manufacturing compression steps.

Figure 7E:
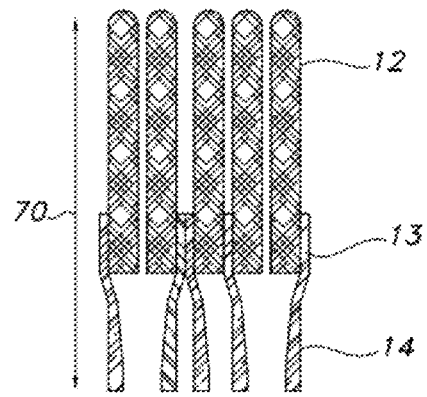
FIG. 7E shows a cross-section view of an alternate embodiment of a portion of a rolled softwind made from a two-ribbon bonded absorbent composite of the present invention (such a softwind being shown in FIG. 9 at 147).

As can be seen in FIG. 7E, in a further alternate embodiment of a softwind, shown in cross- section, the second absorbent material portion 14 may be positioned along only some alternate side edges of the first absorbent material portion 12 in the longitudinal direction 70, such that the "Y" shaped configuration is only formed upon rolling and compression of the bonded absorbent composite.

Figure 7F:
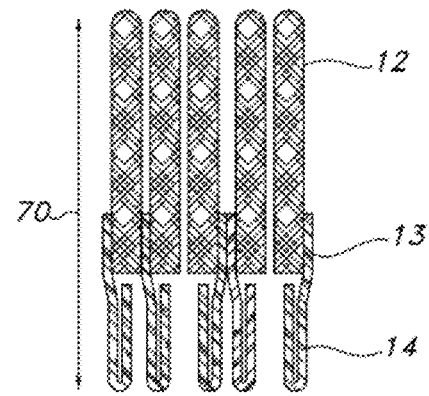
FIG. 7F shows a cross-section view of an alternate embodiment of a portion of a rolled softwind made from a two-ribbon bonded absorbent composite of the present invention (such a softwind being shown in FIG. 9 at 147).

As can be seen in FIG. 7F, in a further alternate embodiment of a softwind, shown in cross-section, the second absorbent material portion 14 may be positioned along only some alternate side edges of the first absorbent material portion 12 in the longitudinal direction 70 and include a partial folded region, such that the "Y" shaped configuration is only formed upon rolling and compression of the bonded absorbent composite (tampon absorbent).

As can be seen in FIG. 7G, in a further alternate embodiment as viewed from a top plan surface of the two bonded ribbons, the first absorbent material portion 12 ribbon may not include the same dimensions in the transverse direction 80 as the second absorbent material portion 14 ribbon.

As can be seen in FIG. 7H, in a further alternate embodiment as also viewed from a top plan surface of the ribbons, the first absorbent material portion 12 ribbon may not include the same orientation in the transverse direction 80 as the second absorbent material portion 14 ribbon.

Figure 8:
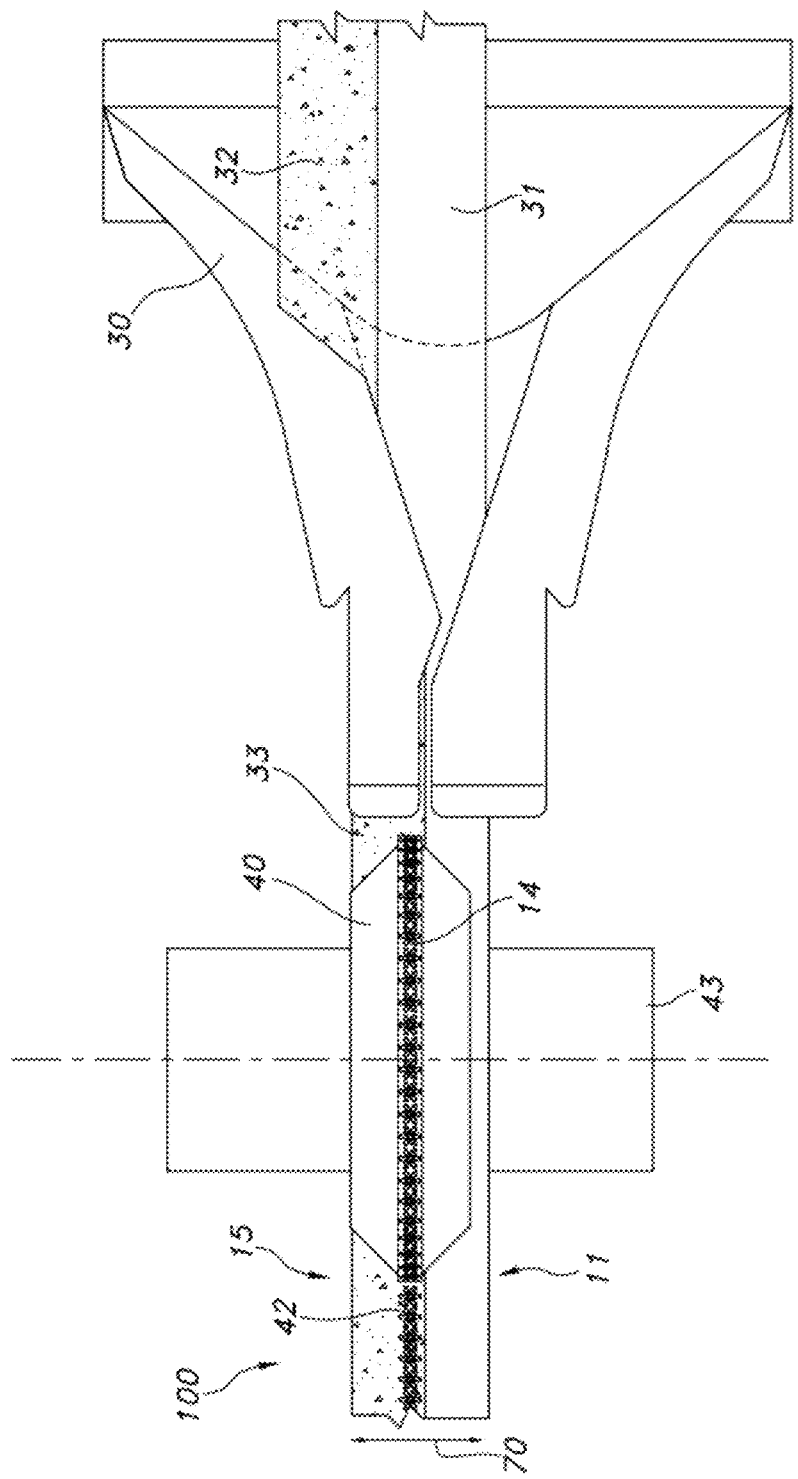
FIG. 8 shows a top view of the formation of a two-ribbon bonded absorbent composite used to prepare the tampon absorbent of the present invention, prior to rolling into a softwind and prior to the introduction of the softwind into a machine to form a tampon blank/the traditional tampon compressing machine for compressing a tampon blank in the jaws of a press.

As can be seen in FIG. 8, the two ribbon-based, bonded absorbent composite 100 which is subsequently rolled and compressed using conventional tampon forming technology, is desirably first formed by the introduction of two separate ribbons 31, 32 into a ribbon calendar and folding board 30. The first ribbon 31, which makes up the first absorbent material portion is fed into the folding board concurrently with the second ribbon 32 which makes up the second absorbent material portion. The folding board proceeds to fold the second ribbon 32 of the second absorbent material portion around the edge and sides of the first ribbon 31, to form the previously described "Y" configuration of the second absorbent material portion around the first absorbent material portion. The second absorbent material portion is folded around the first absorbent at an edge that is perpendicular (transverse) to the longitudinal direction 70 of the absorbent composite 100/tampon absorbent, such that there is some overlap of the absorbent materials, and a portion of the second absorbent portion extends without overlap away from the first absorbent portion 31. This is done along the transverse direction of the bonded absorbent composite. Desirably the folding is conducted so as to allow a space/cavity to be formed between the first and second absorbent portions at the end edge of the first absorbent portion closest to the withdrawal end 15. The paired and folded ribbons 33 are then fed through a set of bonding rolls 40, 43, one on either side of the absorbent composite 100, to bond, desirably through pressure, the two ribbons 31 and 32 together at a bonding region 42 in order to make the bonded absorbent composite. One of the bonding rolls 40 includes a raised bonding surface 14 on which is configured a raised bond pattern such as the flower pattern shown in the figure. As the roll rotates and compresses the folded ribbons between a blank anvil roll 43 positioned on the opposite side of the absorbent composite from the bonding roll 40, the ribbons are compressed and bonded together desirably without the use of a separate heat source or adhesive. In an alternative embodiment, a separate heat source and/or adhesive is also provided to help fuse the ribbons together at the bonding region 42. In still a further alternative embodiment, fibers with a variation in melting points, such as bicomponent binder fibers may be used in one or both of the layers to help in the bonding process. While pressure bonding the ribbons without heat and other bonding mechanisms is preferred in one embodiment, other embodiments can use fiber entanglement techniques, such as needle punching, thermal bonding techniques, ultrasonic bonding and adhesive bonding techniques. In each of these embodiments, a withdrawal cord may be attached to the absorbent composite, such as by bonding or by being looped around it.

Desirably, as shown in FIG. 9, which illustrates a flow chart of manufacturing steps, in order to manufacture a tampon (or tampon absorbent) embodiment from the two ribbon-based, bonded absorbent composite described above, a cover material 16 and the absorbent material portions 12, 14 ribbons are, in a manufacturing step 91, passed through a loop of a withdrawal string 34, having been run through the folding station described above. The cover sheet 16 is adhered to the ribbons by sealing lines 140. Once the product is folded and bonded as described in connection with FIG. 8, the bonded absorbent composite is looped around, in a manufacturing step 92, the withdrawal string 34 positioned in a direction parallel 145 to the longitudinal direction 70 to begin production of a softwind 147. Once the softwind 147 (or tampon blank) has been rolled into an expanded cylinder in a manufacturing step 93, the softwind 147 and cover is then passed through a traditional tampon compression process (jaws of a tampon press) to compress the softwind 147 into a finished-processed tampon 148.

In one embodiment, to prepare a tampon of the present invention, the following method may be used. Generally, first is provided the first absorbent material portion (ribbon) 12. The second absorbent material portion ribbon 14 is placed on the first absorbent material and folded around a transverse edge of the first absorbent portion, to form an absorbent composite, and the composite is bonded at a bonding region of overlap of the two portions, along the composite transverse direction. Next, the absorbent composite may be optionally provided with a cover 16 described above. Once the absorbent composite is folded and bonded, it is formed into a generally cylindrical shape, with a method known to those skilled in the art, such as radially winding the bonded absorbent composite. To radially wind the bonded absorbent composite, a spindle is placed on both sides of the bonded absorbent composite. The spindle is rotated in a direction to form a roll. Once the bonded absorbent composite is formed into a generally cylindrical shape, the bonded absorbent composite is compressed to increase the density of the bonded absorbent composite, thereby forming the tampon or tampon absorbent, having generally uniform diameter, except for the insertion tip.

A specific method of producing a tampon of the invention may also include the steps of first providing a ribbon of a first absorbent material and a second absorbent material, each having a longitudinal direction and transverse direction, positioning the second absorbent material ribbon such that one of its edges is juxtaposed over the edge of the first absorbent material ribbon in a direction perpendicular (transverse) to the longitudinal direction of each of the ribbons, thereby forming an overlap of the two ribbons, folding the second absorbent material ribbon around the edge of the ribbon of the first absorbent material, such as by means of a folding plate, bonding the first absorbent material ribbon to the second absorbent material ribbon at the overlap thereby forming a bonding region, rolling the bonded absorbent composite material ribbons about an axis that is located parallel to the longitudinal direction of the bonded ribbons to form a tampon roll or cylinder, commonly referred to as a tampon blank, inserting the tampon blank into a tampon pressing section of a press commonly used for manufacturing a tampon, and finally pressing essentially radially the tampon blank in the press jaws to form a tampon. Such tampon forming compression devices are available from companies such as Ruggli Ltd. from Switzerland and are offered commercially under the designation CL-3.

Two-ribbon based, bonded tampon absorbent composites as described above, may be used to form both digital and applicator type pledgets for tampons. However, it should also be recognized that additional embodiments of the invention include non-wound pledgets with three absorbent regions along the tampon absorbent longitudinal direction. Such alternate absorbent pledgets include "W" folded, "V" folded, chevron-shaped and cup-like absorbent structures, as described in U.S. Pat. No. 6,837,882 to Agyapong et al.; U.S.20080132868 to Jorgensen et al.; U.S. Pat. No. 6,740,070 to Agyapong et al.; U.S. Pat. No. 7,677,189 to Kondo et al.; and U.S. 2010/0114054 to Mueller et al., each of which is hereby incorporated by reference thereto in its entirety.

For example, it is contemplated that for "W" or chevron pledget configurations, the first absorbent portion material can be comprised of the "W" or chevron material, and a second absorbent portion material can be attached at the withdrawal end of the "W" or chevron pledget prior to folding and/or compression steps. Such second absorbent portion material can be attached prior to, or after the attachment of a withdrawal string, via known methods such as weaving/stitching, needle punching, hydroentangling, adhesive, thermal, or pressure bonding methods. As with many of the previous embodiments, it is contemplated in one embodiment of the "W" or chevron-type pledget, for the second absorbent portion material to be wrapped around the lower (withdrawal end) edge of the first absorbent portion material (formed from the "W" or chevron) such that there is partial overlap of the first absorbent and the second absorbent portion materials, with three distinct absorbent regions being formed, those being a first absorbent region of the "W" or chevron material, a middle region of the overlap of the "W" or chevron material and the second absorbent material, and a third region (in the longitudinal direction), of the second absorbent material.

It is similarly contemplated that such three absorbent region structure can be manufactured using a cup-like tampon pledget. In such a structure, which typically involves the overlapping of perpendicular absorbent layers, it is contemplated that the lowest layer beneath any overlapping layers can include the second absorbent portion material such that the base of the cup would be comprised of the second absorbent portion material upon manufacture, which is bonded (using any of the previously described methods) at overlapping regions to the sides of the finished cup configuration. The upper overlapping layers would comprise the first absorbent portion material. The second absorbent portion material would extend lower in the final cup configuration than the traditional overlapping layers. In a second embodiment, a hole can be cut through the upper overlapping layers to allow for fluid/liquid to pass through the cup to the second absorbent portion material layer below.

Materials

Each of the first and second absorbent material portions 12 and 14 of the absorbent composite desirably contain absorbent materials, in particular, fibrous absorbent materials. Examples of such absorbent materials include materials, such as, cellulosic fibers such as wood pulp, cotton, rayon, viscose, LYOCELL® which is from the Lenzing Company of Austria, or mixtures of these or other cellulosic fibers. Natural fibers can include a variety of fibers, such as wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Crimping may be imparted to the fibers, e.g., by conventional means. Curl may be imparted to the fibers, e.g., by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid or other polycarboxylic acids. Pulp may also be stiffened by the use of heat or caustic treatments such as mercerization. Examples of these types of fibers include NHB41 6 which is a chemically cross-linked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc. of Memphis, Tenn., has a chemical treatment that sets in a curl and twist, in addition to imparting added dry and wet stiffness and resilience to the fiber. Another suitable pulp is Buckeye HP2 pulp, and still another is IP Supersoft from International Paper Corporation.

For the cellulosic fiber (e.g., viscose, rayon, etc.), the fibers in one embodiment can have a staple length of between about 5 mm to about 50 mm. The fibers in one embodiment can have a denier of between about 2 to about 6. Denier is a unit of fineness of yarn based on a standard of 50 milligrams (mg) for 450 meters of yarn. The fibers can have a circular, a bi-lobal, a tri-lobal cross-sectional configuration, or some other cross-sectional configuration known to those skilled in the art. The bi-lobal configuration has a cross-sectional profile which looks like a dog bone while the tri-lobal configuration has a cross-sectional profile which looks like a "Y". Such fibers are available from Kelheim Fibres, Germany, under the Galaxy designation. The fibers can also be bleached, if desired.

When cotton fibers are used, the cotton fibers in one embodiment can have a staple length of between about 5 millimeters (mm) to about 30 mm. The cotton fibers can generally have a fiber size of between about 150 microns to about 280 microns. The cotton fibers can also be bleached if desired. Bleaching will make the cotton fibers whiter in appearance.

In addition to the above absorbent fibers, each of the layers of the absorbent composite may optionally contain other fibers, which are known in the art as binder fibers. Binder fibers typically have a fiber component which will melt or fuse to other fibers in each absorbent layer. Binder fibers may be natural fibers or synthetic fibers. Synthetic fibers include those made from polyolefins, polyamides, polyesters, rayon, acrylics, viscose, superabsorbents, LYO-CELL® regenerated cellulose and any other suitable synthetic fibers known to those skilled in the art. Many polyolefins are available for fiber production, for example polyethylenes such as Dow Chemical's ASPUN® 681 1A linear low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENE® PD 3445 polypropylene and Montell Chemical Co.'s PF304. Another fiber could be a bi-component polyester sheath and polyethylene core and known as T255 made by Trevira of Germany. Other meltable bicomponent fibers are available from Unitika of Japan, such as for example Unitika MELTY 4080, and 6080 fibers, having either polyester sheaths or cores and polyethylene sheaths or cores. Alternative binder fibers are available from Fibervisions under the designation ETC Bounce fiber line, such as PET/PE fibers of about 2.2 dtex and 40 mm staple fiber length. Other polyolefins are also available. Suitable rayon fibers are 1.5 denier Merge 18453 fibers from Accordis Cellulose Fibers Incorporated of Axis, Ala. The fibers can be treated by conventional compositions and/or processes to enable or enhance wettability.

Various methods know to those skilled in the art can be used to prepare each of the layers of the absorbent composite. Known methods such as airlaying, carding, wetlaying, hydroentangling and other known methods may be used to form the individual absorbent layers of the absorbent composite. In one embodiment of the present invention, at least one of the layers is prepared using an airlaying process, wherein the airlaid fibers contain a first fiber and a second fiber, wherein the first fiber is a binder fiber and the second fiber is an absorbent fiber.

In the present invention, the first absorbent material portion 12 may be prepared from any of the absorbent materials described above. The first absorbent portion may be prepared using a carding process, an airlaying process or any other process known to those skilled in the art. The first absorbent portion may or may not contain binder fibers. In one embodiment of the present invention, the first absorbent portion is prepared from a conventional ribbon of an absorbent material which is currently used in tampon productions. As an example, the first layer may be prepared form a carded airlaid web of cotton, rayon or a mixture thereof, with or without the presence of binder fibers. In an alternative embodiment of the present invention the first absorbent portion may include 100 percent regenerated cellulosic fiber, natural fibers, or synthetic fibers such as viscose, rayon cotton or thermoplastic fibers, or mixtures thereof. Desirably, the first absorbent is made of 100 percent trilobal rayon fibers, for example Galaxy VY fibers made by Kelheim Fibres. In one embodiment, the basis weight of such first absorbent portion may be between about 100 to 250 gsm, with a density of such portion desirably between about 0.04 to 0.08 g/cc, and demonstrating a Syngina absorbency of desirably between about 4.3 to 5.5 g/g.

In one embodiment of the present invention, the second absorbent material portion may be prepared from a mixture of the one or more of the absorbent fibers described above and a binder fiber. One exemplary material which may be used in the second layer of the present invention is described in patent application PCT/EP2004/006441 titled: "Airlaid Process With Improved Throughput", filed Jun. 16, 2003, published Dec. 29, 2004 as WO2004/113608, which is owned by the same assignee as this application and which is incorporated herein by reference in its entirety.

In a further embodiment, the second absorbent material portion 14 can be made from 100 percent regenerated cellulosic fiber, natural fibers or synthetic fibers for example viscose, rayon, cotton or thermoplastic fibers or mixtures thereof. Desirably in one embodiment, the second absorbent material portion is made of a mixture of regenerated cellulose for example Galaxy VY blue fibers and thermoplastic binder fibers such as for example Unitika 6080 PET/PE 2.2 dtex fibers of approximately 40 mm length. Desirably the basis weight of the second absorbent material portion 14 is between about 15-300 gsm, more desirably between about 40 to 100 gsm. Desirably the density of such second absorbent portion is between about 0.03 to 0.3 g/cc, more desirably between about 0.06 to 0.12 g/cc. In one embodiment, the second absorbent portion demonstrates a Syngina absorbency of about 3.5 to 5.0 g/g. Desirably the fibers are blended in a ratio of between about 50 percent regenerated cellulose/50 percent binder fiber to about 90 percent regenerated cellulose/10 percent binder fiber, more desirably at a ratio of 80 percent regenerated cellulose to 20 percent binder fiber. In a desired embodiment, both the first absorbent material portion 12 and the second absorbent material portion 14 are hydrophilic, with viscose fibers being permanently hydrophilic and binder fibers being treated with a hydrophilic finish. Such materials may be available from Sandler AG of Germany.

As noted, in addition to the two absorbent material portions 12 and 14, the absorbent composite may also be provided with a cover material 16. The cover prevents the fibers from the absorbent composite of the tampon from directly contacting the inner walls of a woman's vagina. This feature can assist in preventing fibers from being left behind in the vagina after the tampon 10 is removed. This feature may also impact the feel of a tampon at the time of insertion. The cover material 16 can also be tucked into the withdrawal end of the tampon so as to surround and enclose the fibers. The cover can also be constructed from a heat-sealable material to assist in bonding it to the fibers, such as by heat and/or pressure. The cover can be formed from a nonwoven material such as a polyolefin, particularly polypropylene or polyethylene. A suitable material is a spunbond material. Suitable methods and materials for the production of tampons with cover materials are well known to those skilled in the art and will therefore not be further described.

The cover material 16 can be formed as a rectangular sheet and may have a length and a width which are sized so that the cover 16 can wrap completely around the outer periphery of the bonded absorbent composite 12 and 14, when the bonded absorbent composite is rolled. Preferably, the cover 16 will have a length which is equal to or greater than the circumference of the rolled and bonded absorbent composite before compression and will have a width which is about equal to or greater than the outside periphery of the rolled bonded absorbent composite. By so sizing the width of the cover 16, the cover 16 will be able to wrap completely around the outer exterior surface of the bonded absorbent composite and be overlapped upon itself. The liquid-permeable cover 16 can be bonded along the entire length of the overlap region by using an impulse sealer or some other type of sealing mechanism. Alternatively, the cover 16 can be spot bonded at spaced apart points or lines along the overlap region, if desired. The cover 16 can be bonded to either itself and/or to the bonded absorbent composite material portions 12 and 14 using heat, pressure, heat and pressure, ultrasonic, adhesives, glue, or any other known bonding technique.

The liquid-permeable cover 16 can be formed from woven or nonwoven material having a porous substrate. Woven material includes textile fabrics which can be made from rayon, cotton, polyolefins or other synthetic yarns. The synthetics can be either staple or continuous filaments. The cover 16 may be in one embodiment a 12-33 gsm polypropylene spunbond. The nonwoven materials can also include bonded carded webs and hydro entangled webs. Spunbond and bonded carded webs are commercially sold by Kimberly-Clark Corporation, having an office located at 401 North Lake Street, Neenah, Wis. 54956. Another nonwoven material which can be used as the cover 16 is formed from 100 percent polyester fibers held together by a binder. This material is known as powder-bonded-carded web (PBCW). PBCW is commercially available from HDK Industries, Inc. having an office at 304 Arcadia Drive, Greenville, S.C. 29609. The cover 16 can further be formed from an apertured thermoplastic film having either a two-dimensional or a three- dimensional thickness. Apertured thermoplastic films are available from several commercial vendors including Pantex Sri, Pantex Sud srl, Via Terracini snc, having an office at 51031 Agliana, Pistoia, Italy and Applied Extrusion Technology having a mailing address of P.O. Box 582, Middleton, Del. 19709.

The liquid-permeable cover 16 can be treated with an aqueous solution to reduce frictional drag, to enhance the tampon's wettability and to enhance the ease of insertion into and withdrawal from a woman's vagina. The cover 16 can be treated either before being rolled up with the bonded absorbent composite portions 12 and 14 or after the cover 16 has been positioned about the exterior surface of the bonded absorbent composite. The different types of aqueous solutions which can be used are known to those skilled in the art. One particular type of aqueous solution is taught in U.S. Pat. No. 5,533,990 to Yeo, entitled "TAMPON EXHIBITING LOW FRICTIONAL DRAG." This patent is assigned to Kimberly-Clark Worldwide, Inc. and is incorporated by reference and made a part hereof.

The tampon 10 may further include a withdrawal string 34 for assisting in removing the tampon 10 from the woman's vagina. In one embodiment, the withdrawal string 34 is looped around the bonded absorbent composite material portions 12 and 14. Alternatively, the withdrawal string may be attached to the bonded absorbent composite, or material portions thereof 12 and 14. One method of attaching the withdrawal string 34 is to form an aperture or hole through the absorbent composite ribbons. The withdrawal string 34 is then threaded through the aperture and looped upon itself so as to cinch it secure to the absorbent composite material portions 12 and 14. The free ends of the withdrawal string 34 are then tied in a knot to assure that the withdrawal string 34 will not separate from the absorbent composite material portions 12 and 14. The knot also serves to prevent fraying of the withdrawal string 34 and to provide a place or point where a woman can grasp the withdrawal string 34 when she is ready to remove the tampon 10 from her vagina. It should be noted that the withdrawal string 34 can be secured to and/or attached to various areas of the tampon 10 and can pass through at least one of the absorbent material portions 12, 14. The withdrawal string 34 can also be attached either before the mass of absorbent composite 12 and 14 (tampon absorbent) is compressed or after it is formed into the tampon.

The withdrawal string 34 can be constructed from various types of threads or ribbons. A thread or ribbon may be made from 100 percent cotton fibers and/or other materials in whole or part. The string may be bonded to the tampon absorbent, with or without tying before or as the tampon absorbent is being formed into the generally cylindrical shape. In this way, there is no need (or less need) for tying the string to the tampon and better assurance that the string will stay in place and attached to the tampon before, during use and during withdrawal of the tampon till it is ready for disposal. Advantageously and as with the absorbent composite portion materials 12, 14, the string 34 may include bondable binder material, e.g., the same type of material compositions as for the absorbent composite portion materials 12,14 or those with similar bonding characteristics. As such, the string may be a plurality of string fibers including at least a first type of string fiber being bondable to adjacent fibers and where the string is autogenously bonded with the mass of absorbent portion material.

The withdrawal string 34 should have a length which extends beyond the end of the tampon 10 from between about 51 mm to about 203 mm, preferably from about 102 mm to 152 mm, and most preferably, about 127 mm. The withdrawal string 34 can be dyed and/or treated with an anti-wicking agent, such as wax, before being secured to the bonded absorbent composite. The anti-wicking agent will facilitate and prevent body fluids from wicking along the withdrawal string 34 and contacting the inner surface of a woman's undergarment. A dry, clean withdrawal string 34 is preferred by the user, especially when she goes to remove the tampon 10 from her vagina. Depending upon the desired absorbency one desires in the finished tampon, the basis weight of the first and second absorbent portions can vary. For example in one embodiment, the first and second absorbent material portions (12, 14) are targeted to have a total basis weight of between about 100 and 350 gsm. Typically, the formation process is controlled to produce a total first and second absorbent sheet with a width of between about 40 mm to about 60 mm, preferably about 50 mm.

The basis weight and/or the length of the tampon 10 can also be adjusted to form different size tampons. Typically, the total length of the first and second absorbent material portions together, can vary between about 25 and about 60 mm, depending on the required absorbency and basis weight. The tampon absorbent 90 of the present invention can be used to form a digital tampon or a tampon absorbent in an applicator tampon, having a separate applicator which is used to insert the tampon 10 into a woman's vagina, and as are generally known in the art.

Example:

A softwind was prepared by a method previously described, and of the following materials. The first absorbent portion ribbon material was manufactured from 100% trilobal fiber rayon (Galaxy as previously noted) and including a wave/honeycomb compression pattern as previously illustrated in FIG. 5 as 28. The basis weight of the first absorbent portion ribbon material was 165 gsm. The second absorbent portion ribbon material was manufactured from trilobal blue rayon (70-80%) and a bicomponent staple binder fiber (core/sheath) of PET/PE composition (20-30%) and including a diamond bond pattern of spaced spots, as also previously described and illustrated in FIG. 5 at 29. The basis weight was 60 gsm. A bonding pattern of staggered dots, as previously described, was used to bond the first absorbent portion material ribbon to the second absorbent portion ribbon material. A traditional withdrawal string (PET/Viscose yarn) was used in the manufacture and wrapped around the absorbent ribbons. A 12 gsm PET/PE staple fiber TBCW coversheet was included in the tampon. A 70 micron thick cross-section of the produced softwind was then prepared for viewing using the following procedure.

One sample of each type (a softwind and a process-complete/finished tampon made of a compressed softwind) was vacuum infiltrated with Epo-fix embedding epoxy following standard infiltration procedures and mixing epoxy as per manufacturer's directions. The epoxy was allowed to cure overnight at room temperature. The embedded samples were sledge microtome sectioned (a Reichert-Jung Polycut E was used but other microtomes of sledge design will suffice) at 70- and 40-micrometers thickness. Sections were mounted in Epo-fix resin with coverslips. Sections were then photographed using transmitted darkfield illumination by macrophotography and transmitted brightfield illumination with a variety of microscopes. However, for 70 micron samples a Nikon Coolpix 8700 with a 8.9-71.2-mm lens was utilized. Image capture procedures were specific to the method and microscope but standard for that method and microscope. Documentation included image capture of a ruler at the same magnification. A scale bar was transferred to each image so the magnification of the image can be calculated from the scale bar no matter what additional scaling is given to the image.

Figure 10:
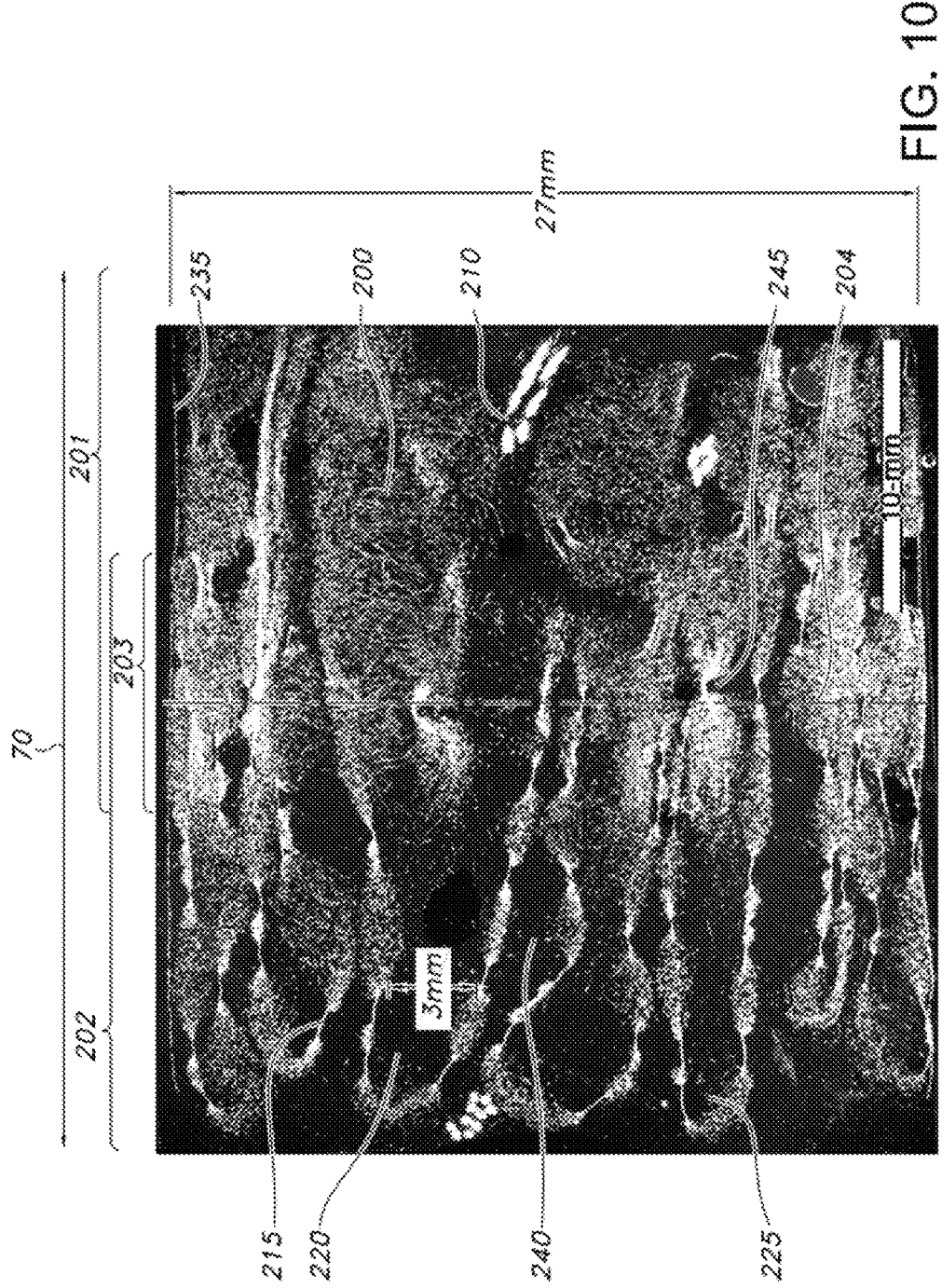
FIG. 10 shows a photomicrograph of a 70 micron thick sample of a cross-section of a softwind tampon absorbent of the present invention.
Figure 11:
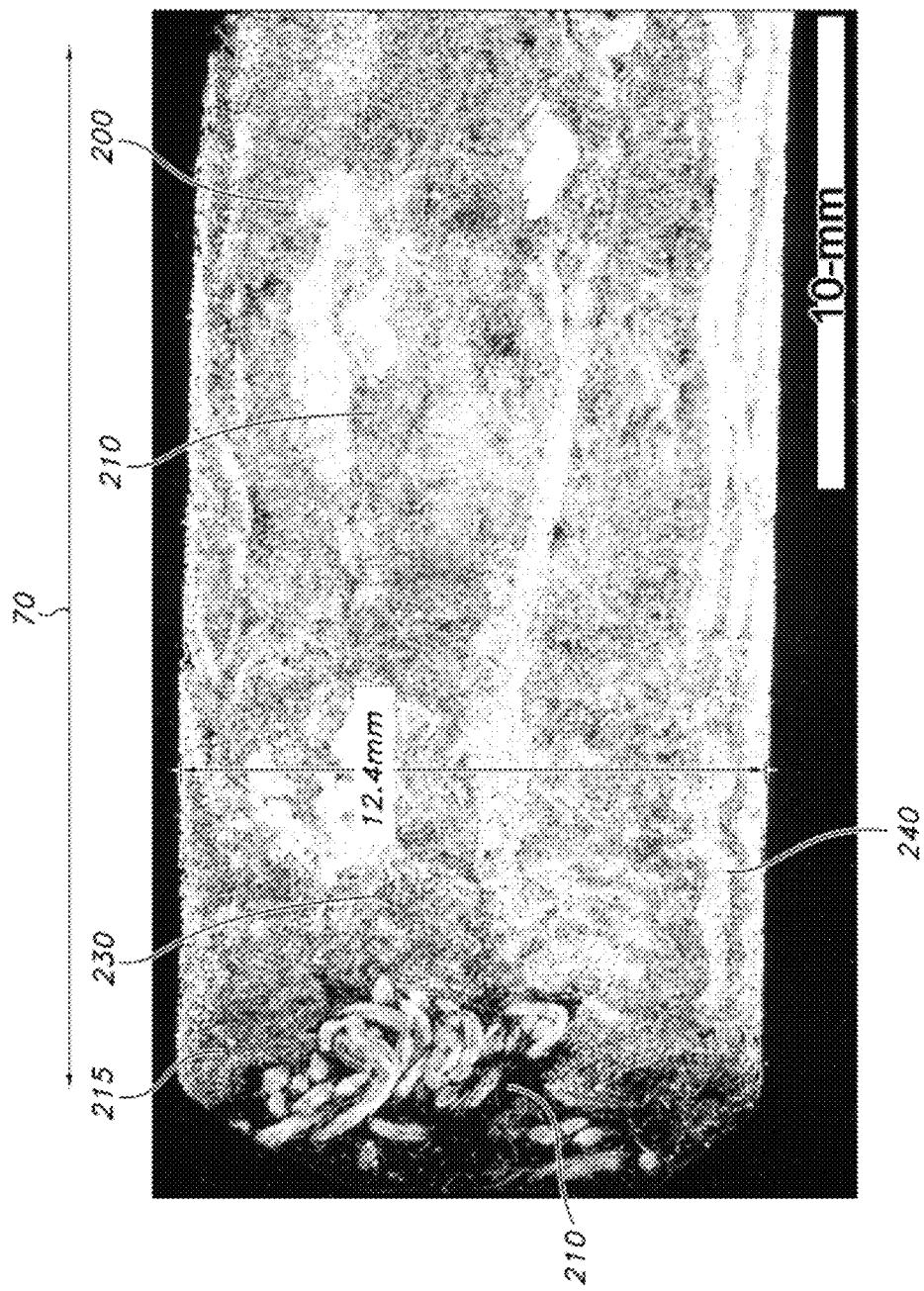
FIG. 11 shows a photomicrograph of a 70 micron thick sample of a cross-section of a radially compressed softwind (as a finished-processed digital tampon) of the present invention.

Following cross-sectional sample preparation and photography taken (samples 70 microns), as are shown in FIGS. 10 and 11, a review of the images was conducted. As can be seen in the photomicrograph shown in FIG. 10, which depicts a cross-section image of an uncompressed softwind, also stylistically shown in FIG. 9 at 147, the softwind includes a first absorbent material portion 200 in first absorbent regions 201, as well as a second absorbent material portion 225 in second absorbent regions 202. The second absorbent material portion is folded around the edges of the first absorbent material portion to thereby create a cavity 220 having varied widths, with one in particular being approximately 3 mm. A cover 235 is shown along the side edge of the softwind. The withdrawal string is also visible 210. Spaces can be seen 240 between adjacent second absorbent portion folds/lobes, as well as adjacent bonding elements in the bonding region. It is theorized that these spaces provide for more surface area absorbency, as well as the cavities, upon expansion of the compressed tampon absorbent in use. The bond elements 245 in the bonding region 203 can be seen, as relatively flattened areas. Additionally, parts of the diamond bond pattern 215 can be seen in the second absorbent material portion. The approximate width of the softwind in the transverse direction is 27 mm. The first absorbent material region is generally shown as 201 and extends outside the image in the longitudinal direction 70, overlapping the second absorbent material region 202 at the bonding region 203, which include the bond points 245. An imaginary line 204 indicates the general vicinity of the bond elements in the bonding region.

A softwind as described above, was then radially compressed using a tampon compression system, and cross-section images were prepared, again of 70 micron thick samples, one of which is seen in FIG. 11. As can be seen in FIG. 11, the compressed tampon now has a width dimension in the transverse direction of approximately 12.4 mm. The withdrawal string 210 can be seen at two locations. The first absorbent material portion 200 and the second absorbent material portion 230 have been compressed such that spaces between them and between folds have been eliminated or noticeably reduced. The compressed layered folds 240 will re-expand upon use, in theory to produce spaces that were present in the uncompressed softwind.

Without being bound by theory, it is theorized that construction of a tampon absorbent as described, provides various comfort attributes to a potential user. The female vaginal canal is known to include a bend or kink above the pelvic floor muscles, rather than being formed in a straight line. As a result, a tampon absorbent which demonstrates the ability to bend along its longitudinal direction provides enhanced comfort during use, and bends to conform to the topographical bend in the vaginal canal. Such ability to bend results from the inclusion of three separate regions of stiffness/absorbency along the tampon absorbent longitudinal direction, allowing the tampon absorbent to bend/flex at or near a central more stiffened overlapping region (in the longitudinal direction), the bonding region between the first absorbent portion and the second absorbent portion. Further, the reduced "expansion capacity" second absorbent portion provides comfort during tampon withdrawal, but likely opens somewhat upon insertion.

All publications, patents, and patent documents cited in the specification are incorporated by reference herein, as though individually incorporated by reference. In the case of any inconsistencies, the present disclosure, including any definitions herein, will prevail. While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

What is claimed is:

1. A tampon for insertion into a vaginal cavity, said tampon comprising: a tampon absorbent having a longitudinal direction including an insertion end and a withdrawal end and an outer exterior surface, said tampon absorbent further comprising, in the longitudinal direction of the tampon absorbent, a first absorbent region at said insertion end, the first absorbent region comprised solely of a first absorbent material for storing body fluid and demonstrating a first expansion capacity, a second absorbent region at said withdrawal end, the second absorbent region comprised solely of a second absorbent material for storing body fluid and demonstrating a second expansion capacity wherein the second absorbent material is different from the first absorbent material, and a third absorbent region situated between the first absorbent region and the second absorbent region, the third absorbent region comprised of both the first absorbent material and the second absorbent material, wherein the first absorbent region is bonded to the second absorbent region at the third absorbent region such that the second absorbent region overlaps the first absorbent region at the third absorbent region, and the third absorbent region is situated along the tampon absorbent longitudinal direction between the insertion end and the withdrawal end;

a withdrawal string attached to and extending from said withdrawal end of said tampon absorbent; and a cover material which wraps completely around the outer exterior surface of the tampon absorbent.

2. The tampon of claim 1 wherein said first expansion capacity is greater than said second expansion capacity.

3. The tampon of claim 1 wherein a hollow cavity is adjacent said first absorbent region towards said tampon absorbent withdrawal end, said cavity defined by the second absorbent region.

4. The tampon of claim 1, wherein said third absorbent region includes an exposed edge of said second absorbent material that is of a linear, zigzag, wave, or curvilinear design.

5. The tampon of claim 1 wherein said third absorbent region demonstrates a third expansion capacity that is different from both said first and second expansion capacities.

6. The tampon of claim 1 wherein at least one of the absorbent regions is of a different color than the other absorbent regions.

* * * * *